United States Patent
Schron

(10) Patent No.: US 7,421,608 B2
(45) Date of Patent: Sep. 2, 2008

(54) METHOD AND SYSTEM FOR OPERATING A DENTAL OPERATING CHAIR CONNECTED TO A COMPUTER

(75) Inventor: Roger Schron, Birkenau (DE)

(73) Assignee: Sirona Dental Systems GmbH, Bensheim (DE)

( * ) Notice: Subject to any disclaimer, the term of this patent is extended or adjusted under 35 U.S.C. 154(b) by 483 days.

(21) Appl. No.: 10/733,301

(22) Filed: Dec. 12, 2003

(65) Prior Publication Data

US 2004/0183352 A1 Sep. 23, 2004

Related U.S. Application Data

(63) Continuation of application No. PCT/DE02/02115, filed on Jun. 12, 2002.

(30) Foreign Application Priority Data

Jun. 12, 2001 (DE) ................ 101 33 593

(51) Int. Cl.
G06F 1/00 (2006.01)
G06F 3/00 (2006.01)
A61H 1/00 (2006.01)

(52) U.S. Cl. .......... 713/500; 713/300; 710/5; 601/1

(58) Field of Classification Search .............. 606/1; 710/5; 713/500, 300
See application file for complete search history.

(56) References Cited

U.S. PATENT DOCUMENTS

| | | | | |
|---|---|---|---|---|
| 4,908,612 A | * | 3/1990 | Bromley et al. ........... | 345/159 |
| 5,300,926 A | * | 4/1994 | Stoeckl ................ | 345/157 |
| 5,467,002 A | * | 11/1995 | Brooks ................ | 318/553 |
| 5,484,188 A | * | 1/1996 | Stoeckl ................ | 297/408 |
| 5,910,139 A | * | 6/1999 | Cochran et al. .......... | 606/1 |
| 5,938,740 A | * | 8/1999 | Chang ................ | 710/5 |
| 5,947,729 A | | 9/1999 | Bell .................... | 433/98 |
| 5,961,610 A | | 10/1999 | Kelly et al. ............ | 709/300 |
| 6,013,882 A | * | 1/2000 | Boetzkes ............... | 200/86.5 |
| 6,179,829 B1 | * | 1/2001 | Bisch et al. ............ | 606/1 |
| 6,278,975 B1 | * | 8/2001 | Brant et al. ............ | 704/275 |
| 6,798,396 B2 | * | 9/2004 | Gemunder et al. ....... | 345/156 |

FOREIGN PATENT DOCUMENTS

| | | |
|---|---|---|
| DE | 41 25 137 A1 | 2/1993 |
| EP | 0 845 247 A2 | 6/1998 |
| EP | 0 993 808 A2 | 4/2000 |
| EP | 0 734 689 B1 | 2/2003 |

* cited by examiner

Primary Examiner—Thomas Lee
Assistant Examiner—Vincent T Tran
(74) Attorney, Agent, or Firm—Dykema Gossett PLLC

(57) ABSTRACT

A method and a system for operating a dental operating chair connected to a computer, comprising operating elements and/or state indicators arranged on the dental operating chair, an interface via which the information is transmitted from the dental operating chair to the computer, in the form of function codes, by the operating elements and/or state indicators, and a memory region on the computer, in which at least one action associated with a function code is stored. To adapt the operating elements or the operating surface, software for managing the function codes is provided on the computer, by which the action associated with the function codes and stored in a configuration file is initiated. The allocation of the function codes of the operating elements and/or the state indicators of the dental operating chair to the PC actions can be configured by changing the configuration file.

12 Claims, 2 Drawing Sheets

METHOD AND SYSTEM FOR OPERATING A DENTAL OPERATING CHAIR CONNECTED TO A COMPUTER

CROSS REFERENCE TO RELATED APPLICATION

This is a continuation of International Application PCT/DE02/02115 filed Jun. 12, 2002, which designated the U.S. All priorities are claimed.

TECHNICAL FIELD

The invention relates to method and system for the operation of a dental chair connected to a computer (PC).

The integration of a computer-controlled PC monitor in dental treatment areas enabling the display of PC applications at the chairside usually entails operation of the installed computer from a position near the dental chair.

BACKGROUND OF THE INVENTION

The use of conventional PC peripheral input devices, eg, a mouse or keyboard, is not ergonomic for hygienic and handling reasons. For this reason, operations such as un-parking and parking of a video camera integrated in the dental chair or the actuation of footswitches associated with this application are transmitted via a computer interface of the dental chair to a computer interface of the computer, where they initiate certain pre-programmed functions in PC applications when the latter are running and are designed to carry out such functions.

Thus images, for example, of the oral cavity of a patient, which are created by a video camera and displayed on a monitor of the computer are transmitted via an interface in the patient's chair to the computer on account of commands issuing from a footswitch connected to the patient's chair, which commands cause a corresponding storage command to be carried out within the application.

Other operations of the PC application are only possible by way of standard input devices of the PC, usually the keyboard and mouse.

U.S. Pat. No. 5,961,610 discloses a medical image projection system, which exhibits the possibility of programmability. Among other features, it is possible to display a number of images in a single area without overlapping. And it is possible to write a script in a window to influence the order of program events. This script is to be regarded as a small independent program, which can be checked for proper running in a debugger. The assignment of the function keys is not itself explained, so that it may be assumed that in the prior art it is achieved by fixed programming.

It is an object of the invention to provide a method and system making it possible to effect efficient control of a computer connected to a dental chair.

SUMMARY OF THE INVENTION

This object is achieved by a system and method comprising the features defined in the independent claims. The subclaims refer to further embodiments of the invention.

A system for operating a dental chair connected to a computer, comprising actuating elements and/or status indicators disposed on the dental chair, and comprising a computer interface, via which information is transmitted in the form of function codes to the computer by way of the actuating elements and/or status indicators on the dental chair, and comprising a storage area in the computer in which actions assigned to one or more function codes are stored, is characterized in that software is installed on the computer which is capable of managing these function codes and by means of which the action assigned to the function codes in a saved configuration file is initiated, ie a PC application is opened or closed or an operation is carried out in a running PC application, and that the assignment of function codes associated with the actuating elements and/or status indicators on the dental chair to the PC actions can be configured by modifying the configuration file.

Due to the given freedom of programmability, the computer interface can be utilized by other PC applications within the scope of the commands available therein. When there is a change in the PC application used, the action assigned to the function codes also changes, for example by cueing a corresponding configuration file in which the new assignments are saved.

According to a further embodiment, the software has a dialog box by means of which the assignment can be specified by the user.

According to a further embodiment, the assignment of the actuating element is dependent on the currently active PC application. Furthermore, the actuating element concerned can be assigned to different actions in different PC applications.

The computer interface is advantageously designed such that information on the assignment of the actuating element can be transmitted from the computer to the dental chair and can be made perceptible on the control panel.

A method of controlling a dental chair connected to a computer comprises the steps of actuating an actuating element located on the dental chair and/or activating a status indicator and generating information thereon at the dental chair, transmitting said information in the form of one or more function codes from the dental chair to the computer, comparing the information in the form of one or more function codes with a configuration file in a storage area in the computer and carrying out the action assigned to said information as stored in a configuration file, and is characterized in that the comparison of the information is taken over by software which is designed to manage said assignment and is independent of the PC applications used, which software causes the said action to be carried out, namely opening or closing of a PC application and/or execution of an operation in a running PC application, and that the software is configured by modifying the configuration file via a dialog box, in which the assignment of function codes of the actuating elements and/or status indicator on the dental chair to the action is specified.

Advantageously, the software is adapted to make it possible to store more than one configuration. Furthermore, the action assigned to the actuating element can be dependent on the currently active PC application. According to a further embodiment, the actuating element concerned has different action assignments for different PC applications.

Advantageously, the assignments are displayed on the control panel of the dental appliance. The PC context returned through the computer interface may be displayable, or an application-specific control panel may be shown.

The invention makes it possible to establish a user-configured assignment of operations carried out at the chairside, or of defined changes of status of the dental chair, to certain PC functions. The existing control panel of the dental chair is utilized here for the control of the various PC applications.

The layout of the control panel of the dental chair can be governed by the status of the PC, ie is dependent on which PC application is running, or it may be directly controlled by the PC application itself.

Thus the user is in a position to effect chairside operation and individual configuration of the PC applications used, or even other functions used in the PC network, without the aid of standard PC input devices. Furthermore, the fact that the means for controlling the PC, as are dependent on the PC application used, are displayed on the control panel of the dental chair results in a high operational potential. From the point of view of the user, the operation of the dental appliance and the PC (internally/externally) merge together, combined with the ergonomic operational benefits of the dental chair.

On the one hand the dental chairs are configured in relation to the PC function, whilst on the other hand the control panel of the dental chair can be designed for configuration of PC control means depending on the PC application.

BRIEF DESCRIPTION OF THE DRAWINGS

The invention is explained below in greater detail with reference to an embodiment illustrated diagrammatically in the drawing. In the drawings.

WORKING EXAMPLE

Figure 1:
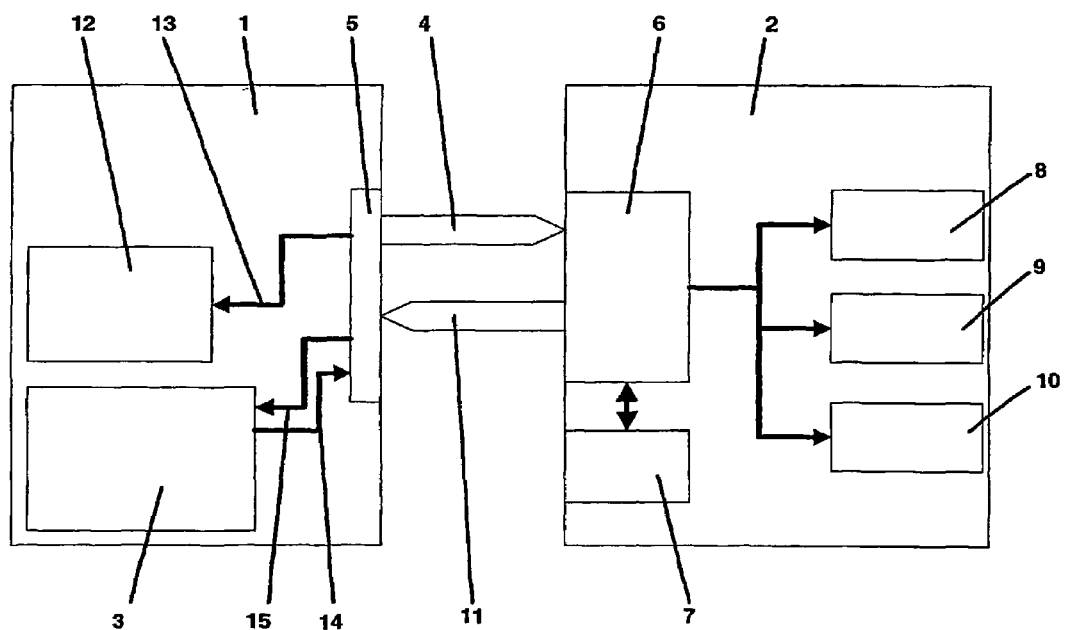
FIG. 1 shows the functional components of a system of the invention and FIG. 2 shows a dental operating chair exhibiting further components of the system.

FIG. 1 shows the functional components of a dental chair 1 equipped with a computer 2. Actuating elements or status changes defined as function keys 3 of a dental chair 1 are transmitted, on activation, as a function code 4 to the PC 2 via computer interfaces 5, 6.

Software managing the computer interfaces starts an action assigned to this function code in a configuration file 7 stored in a storage area in the computer 2, eg, it opens or closes a PC application 8, 9, 10 or initiates some operation in a running PC application.

By means of a dialog box the user can configure the assignment of the function codes of the actuating elements of the dental appliance to certain PC actions.

The assignment of the function keys 3 may be governed by the currently active PC application, ie the actuating elements concerned have different action assignments for different PC applications, to which end information 11 is transmitted via the computer interfaces 6, 5 of the computer 2 to the dental chair 1.

The assignments are displayed, and the PC context returned via the computer interface is indicated according to the design of the control panel 12 of the dental appliance. Furthermore, an application-specific control panel may be displayed.

The PC software managing the interfaces registers the PC context, ie it recognizes the currently active application and relevant changes in the application used. This recognition can be effected, for example, by mechanisms of the PC operating system or alternatively by notification from the currently active application to the PC software. The definition as to which changes of context will specify what function assignments will be allocated to the control panel 12 of the dental chair 1 is a component of the configuration file. New assignments of function codes to PC actions when there is a change in context will be established as specified in the configuration.

Furthermore, the PC context or the function assignment of individual actuating elements 3 can be displayed by conventional display units, but preferably graphically on the control panel 12 of the dental chair. The graphical content of the displays can likewise be allocated in the configuration file, and this information 11 can, when required, be loaded into the dental chair 1 via the computer interface 5, 6, where it is displayed in the control panel 12. For this purpose there is provided a unidirectional signal connection 13.

By the term "control panel" we mean any arrangement which imparts information concerning the operation and status of the dental chair or of the PC and, in particular, makes such information perceptible by display means.

Instead of function keys, an additional switching element, such as a footswitch, can initiate the transmission of function codes to the computer, as may also the recognition of the removal of an instrument intended to be regarded as an indication of state transition. The actuating elements can be integrated in the control panel and cooperate with the computer interface through signal lines 14, 15.

The dental unit may also have its own storage area, the content of which can be modified via the configuration file of the computer and which cooperates with the control panel 12 and the actuating elements 3.

Figure 2:
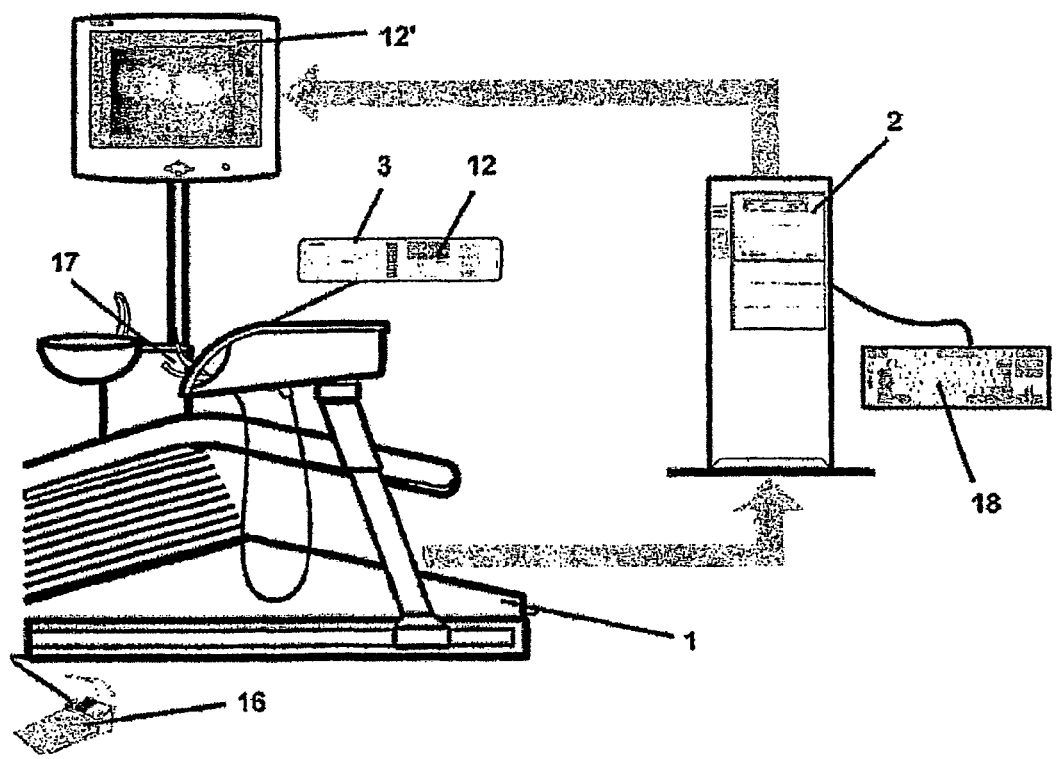

FIG. 2 illustrates a dental operating chair 1 having further components of the system. Thus there are shown an actuating element 3 connected to the dental chair and having a number of keys and displays 12, and a computer 2 having an input keyboard 18 and a monitor 12' connected to the computer so as to display a PC application. Instruments 17 can be controlled by means of a footswitch 16 connected to the dental chair 1.

The method can be set down in the form of a software program as defined in any one or more of the following method claims. A data medium can contain a data structure that is capable of running on a computer to realized a process as defined in one or more of the following method claims.

The following table gives examples of function codes for PC functions as generated in the dental chair and depending on the status of the dental chair:

| Status of the dental chair | PC function controlled |
| --- | --- |
| Chair moves to investigating position | Patient is logged into the software supporting the treatment, and the display shows the history of treatment and planned treatment |
| Chair moves to get-out position | Patient is logged out from the software supporting the treatment, opened patient-dependent data or images are closed |
| Chair moves to pause position (for interrupted treatment) | Software for information for the patient or for entertainment (video, TV) is started |
| Chair leaves pause position | Software for information for the patient or for entertainment is stopped |
| Diverse positions of the chair, unparking and parking of instruments, state of regeneration | Control of an on-line help menu or of operating instructions (tutorial), synchronized by system states of the dental chair |
| Error state of the dental chair | System status of the dental chair including service information are read and sent by email or fax to a preset address for remote diagnosis |
| Actuation of commutator switch and pedal of footswitch (dental chair) | Navigation and activation of a function in the currently active PC application |

| Status of the dental chair | PC function controlled |
| --- | --- |
| Actuation of keys in control panel of dental chair | Activation of any desired functions of currently active application or change in the application to be used |

From the dental chair state transitions are transmitted in the form of function codes irrespective of the status of the PC. Software for the computer interface running on the PC detects the PC context, ie the currently active application, and switches the function configured for said application.

The PC context and also the assigned functions are indicated in the control panel of the dental chair preferably by means of application-specified symbols.

The invention claimed is:

1. A system for operating a dental chair operatively connected to a computer provided separate from a dental chair control unit, comprising, one of actuating elements and status indicators disposed on the dental chair, a computer interface, via which information is transmitted in the form of function codes from the dental chair control unit to the computer by way of the actuating elements, and a storage area in the computer, in which actions assigned to at least one function code are stored, wherein the computer has software capable of managing said at least one function code and by means of which the actions assigned to said at least one function code in a saved configuration file in the storage area is initiated, functions of the software being carried out in a running PC application, and wherein the assignment of said at least one function code associated with the actuating elements or status indicators on the dental chair to prescribed actions are capable of being configured by modifying the configuration file for the software.

2. A system as defined in claim 1, wherein the software includes a dialog box by means of which a user can allocate said at least one function code issuing from said one of the actuating elements and status indicators on the dental chair to predetermined PC actions.

3. A system as defined in claim 1, wherein the assignment of the actuating elements depend on the currently active PC application.

4. A system as defined in claim 1, wherein the actuating elements have different assignments for different PC applications.

5. A system as defined in claim 1, wherein information concerning the assignment of the actuating elements is capable of being transmitted from the computer to the dental chair via the computer interface and is made perceptible on a control panel.

6. A method of controlling a dental chair operatively connected to a computer provided separate from a dental chair control unit, comprising the steps of:

actuating one of an actuating element and a status indicator disposed on the dental chair, and generating information thereon at the dental chair;

transmitting the information in the form of at least one function code from the dental chair to the computer;

comparing the information in the form of said at least one function code with a configuration file in a storage area in the computer; and carrying out an action assigned to predetermined information stored in a configuration file;

wherein the comparison of the information is taken over by software managing said assignment and independent of the PC applications used, by means of which the action is carried out, by opening or closing of a PC application, and wherein the assignment of said at least one function code of the status indicator or actuating element on the dental chair to the action is specified and is configured by modifying the configuration file.

7. A method as defined in claim 6, wherein a user of the software specifies the assignment of said at least one function code issuing from the status indicators on the dental chair to predetermined PC actions in a dialog box.

8. A method as defined in claim 6, wherein the software provides means for storing a number of different configurations.

9. A method as defined in claim 6, wherein the assignment of the actuating element is dependent on the currently active PC application.

10. A method as defined in claim 6, wherein in different PC applications different actions are assigned to the actuating element concerned.

11. A method as defined in claim 6, wherein the assignments are displayed on a control panel of the dental chair.

12. A method as defined in claim 6, wherein a PC context that is returned via a computer interface is indicated on a control panel.

* * * * *